US009867916B2

(12) United States Patent
Schumacher

(10) Patent No.: US 9,867,916 B2
(45) Date of Patent: Jan. 16, 2018

(54) IMPLANTABLE BLOOD CONVEYING DEVICE, MANIPULATING DEVICE AND COUPLING DEVICE

(75) Inventor: Joerg Schumacher, Teltow (DE)

(73) Assignee: Berlin Heart GmbH, Berlin (DE)

( * ) Notice: Subject to any disclaimer, the term of this patent is extended or adjusted under 35 U.S.C. 154(b) by 174 days.

(21) Appl. No.: 13/261,605

(22) PCT Filed: Aug. 10, 2011

(86) PCT No.: PCT/EP2011/004063
§ 371 (c)(1),
(2), (4) Date: May 31, 2013

(87) PCT Pub. No.: WO2012/025199
PCT Pub. Date: Mar. 1, 2012

(65) Prior Publication Data
US 2013/0245360 A1   Sep. 19, 2013

Related U.S. Application Data

(60) Provisional application No. 61/377,678, filed on Aug. 27, 2010.

(30) Foreign Application Priority Data

Aug. 27, 2010   (EP) .................................... 10075373

(51) Int. Cl.
*A61M 1/10*   (2006.01)
*A61B 17/34*   (2006.01)
*A61B 17/00*   (2006.01)
*A61M 1/12*   (2006.01)

(52) U.S. Cl.
CPC ............ *A61M 1/10* (2013.01); *A61M 1/1008* (2014.02); *A61B 17/3415* (2013.01); *A61B 2017/00477* (2013.01); *A61B 2017/00876* (2013.01); *A61M 1/101* (2013.01); *A61M 1/122* (2014.02); *A61M 1/125* (2014.02)

(58) Field of Classification Search
CPC ................................................ A61B 17/3415
USPC ............................................. 600/16; 623/3.11
See application file for complete search history.

(56) References Cited

U.S. PATENT DOCUMENTS

| | | |
|---|---|---|
| 3,510,229 A | 5/1970 | Smith et al. |
| 3,568,659 A | 3/1971 | Karnegis |
| 3,802,551 A | 4/1974 | Somers |

(Continued)

FOREIGN PATENT DOCUMENTS

| | | |
|---|---|---|
| CA | 1008330 A1 | 4/1977 |
| CA | 2311977 A1 | 12/2000 |

(Continued)

*Primary Examiner* — Joseph Dietrich
(74) *Attorney, Agent, or Firm* — Marshall & Melhorn, LLC

(57) ABSTRACT

The invention provides an implantable component which is connectable to a manipulating device in a self-retaining manner by means of a coupling device, which provides a first coupling element and a second coupling element. The implantable component can thus be really positioned by the manipulating device which can, for example, already be connected to the implantable component before a therapeutic procedure and can be separated therefrom again after the surgical procedure. This is in particular advantageous with minimally invasive procedures.

6 Claims, 4 Drawing Sheets

(56) References Cited

U.S. PATENT DOCUMENTS

| | | |
|---|---|---|
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,853,420 A | 12/1998 | Chevillon et al. |
| 5,882,329 A | 3/1999 | Patterson et al. |
| 5,888,241 A | 3/1999 | Jarvik |
| 5,938,672 A | 8/1999 | Nash |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Scmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nusser |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,344,553 B2 | 3/2008 | Opolski et al. |
| 7,393,181 B2 | 7/2008 | McBride et al. |
| 7,467,929 B2 | 12/2008 | Nusser et al. |
| 7,618,435 B2 | 11/2009 | Opolski |
| 7,731,675 B2 | 6/2010 | Aboul-Hosn et al. |
| 7,927,068 B2 | 4/2011 | McBride et al. |
| 7,934,909 B2 | 5/2011 | Nuesser et al. |
| 8,343,029 B2 | 1/2013 | Farnan et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2005/0154417 A1 | 7/2005 | Sepetka et al. |
| 2006/0008349 A1 | 1/2006 | Khaw |
| 2006/0062672 A1 | 3/2006 | McBride et al. |
| 2006/0195004 A1 | 8/2006 | Jarvik |
| 2007/0276352 A1* | 11/2007 | Crocker ............ A61B 10/025 604/500 |
| 2008/0076960 A1 | 3/2008 | Marseille et al. |
| 2008/0132747 A1 | 6/2008 | Shifflette |
| 2008/0154302 A1 | 6/2008 | Opolski et al. |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0093764 A1 | 4/2009 | Pfeffer et al. |
| 2009/0093796 A1 | 4/2009 | Pfeffer et al. |
| 2009/0240326 A1 | 9/2009 | Wilson et al. |
| 2010/0041939 A1 | 2/2010 | Siess |
| 2010/0268017 A1 | 10/2010 | Siess |
| 2011/0190567 A1 | 8/2011 | Farnan et al. |
| 2011/0190707 A1 | 8/2011 | Farnan |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner |
| 2013/0204362 A1 | 8/2013 | Toellner |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 | 4/2009 |
| CN | 101668490 A | 3/2010 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |

(56) References Cited

FOREIGN PATENT DOCUMENTS

| | | |
|---|---|---|
| DE | 69407869 T2 | 4/1998 |
| DE | 29804046 U1 | 6/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 1 | 10/2000 |
| WO | 2001007760 A1 | 2/2001 |
| WO | 2001007787 A1 | 2/2001 |
| WO | 2001083016 A2 | 11/2001 |
| WO | 2003057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | WO 2009/029387 A1 | 3/2009 |
| WO | WO 2009/055651 A1 | 4/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

* cited by examiner

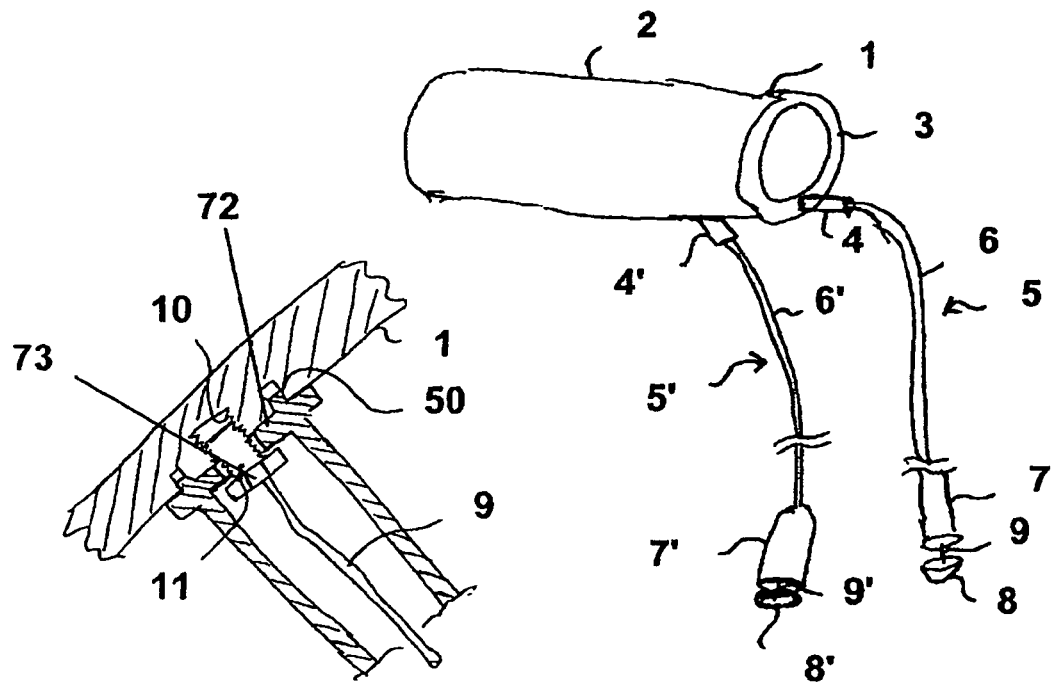
Fig. 1
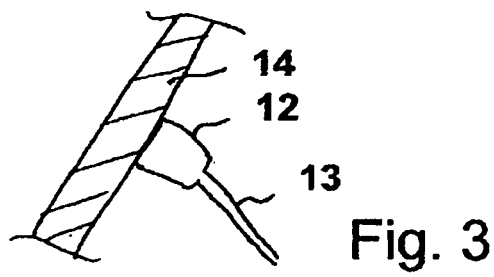
Fig. 2
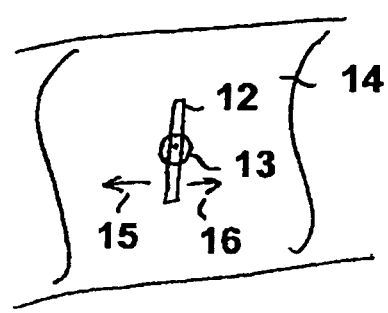
Fig. 3
Fig. 4
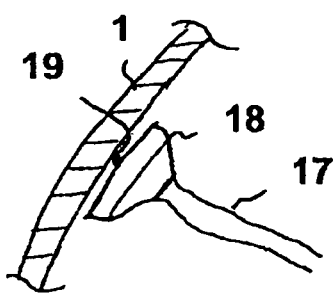
Fig. 5

IMPLANTABLE BLOOD CONVEYING DEVICE, MANIPULATING DEVICE AND COUPLING DEVICE

BACKGROUND OF THE INVENTION

The invention is in the field of medical engineering, in particular implant medicine, and in particular relates to the possibilities of implanting components with a minimal effort using minimally invasive procedures.

Implant medicine allows the use of the most varied units and elements in a patient's body for the replacement of specific organs and body parts in a temporary or permanent manner or the insertion of specific units to support bodily functions.

Such units can usually be put in place in a simple manner with a large opening of the patient's body, but with considerable surgical trauma arising. The reduction of surgical trauma requires smaller procedures, with the openings for introducing components into the body in part only being a little larger or even smaller, with an elastic widening, than the components to be introduced. Corresponding units can be introduced in parts and can also be assembled inside the body.

The minimal invasive introduction often does not allow the direct handling of components by hand so that additional instruments such as forceps are used. However, the use of such holding instruments is also not always simple. The components to be implanted are frequently designed as small as possible and also rounded so as to provide as little irritation as possible in the body, in particular with cardiac assist systems having a plurality of parts which conduct blood. On the other hand, it brings along a difficult management by corresponding holding instruments such as forceps. A precisely targeted positioning or the assembly of individual components in the patient's body is also difficult. This can in particular be the case with cardiac assist systems when pumps, canulae and drive components have to be assembled.

Various aids are known from the prior art for implanting parts of cardiac assist systems into a patient's body.

An apparatus is known from PCT/US2008/081082 having an anchor which can be inserted close to the heart and which is connected to a guide fiber. A tubular hollow body is displaceable toward the anchor on the guide fiber and can be held there by means of a magnetic device.

A handling device for a canula is known from WO 2009/029387 A1 which has a guide body extending through the interior of the canula and a holding body which can be expanded radially in the manner of a cushion to hold the canula. Said holding body can be expanded so far that it jams in the interior of the canula.

BRIEF SUMMARY OF THE INVENTION

Against the background of the prior art, it is the underlying object of the invention to provide a blood-conductive implantable component which effectively cooperates with a corresponding manipulating device to allow a reliable insertion and positioning in a patient's body with minimally invasive surgery. A further subject of the solution is a corresponding manipulating device, a coupling device for the mechanical coupling of an implantable component with a manipulating device as well as the system comprising the component and the manipulating device and a corresponding method for connecting the components to a manipulating device and for separating them.

The object is achieved by an implantable component in accordance with the invention, by a manipulating device for handling such a component, by a coupling device for the mechanical coupling of a component with a manipulating device, by a system comprising at least one implantable component and at least one manipulating device, by a corresponding method for connecting an implantable component to a manipulating device and by a method for separating an implantable component from a manipulating device.

The invention relates to an implantable component which bounds a blood-conductive passage within a human or animal body in operation, which in particular forms a part of a blood conveying device and which has a coupling element which is configured for mechanical coupling to a manipulating device, wherein the coupling between the manipulating device and the component allows a manipulation in all spatial directions. This means that the component is displaceable in freely selectable spatial directions depending on the necessities in handling. In addition, the component can also be rotatable and/or pivotable about different axes, in particular a plurality of axes. These axes can extend inside and/or outside of the implantable component and, for example, also through a coupling element. A fixed-angle connection of the coupling elements to one another in one or more planes, in particular at all sides, can in particular be provided for this purpose.

Such a component can generally be any component usable in a patient's body, in particular a part of a cardiac assist system, a blood pump, a blood pump for coupling to a heart, a valve, a canula, a catheter, corresponding connection systems between these components as well as a medicine dispensing pump.

Many of these components are equipped with particularly smooth and rounded surfaces to avoid lesions on the insertion into or dwelling in a body. This makes the handling by the hand of the surgeon or by grasping forceps difficult. For this reason, in accordance with the invention, a coupling element is provided which is configured for the mechanical coupling of a manipulating device to the component. In this connection, a surgical instrument is, for example, understood as a manipulating device which has, for example, a handle at the proximal end facing the surgeon as well as a shaft and a distal end which is connectable to the coupling element of the component.

For this purpose, a further coupling element which is connectable to the first coupling element fastened to the implantable component or integrated therein can be provided at the distal end of the manipulating device.

A mechanical coupling is thus provided which allows a reliable manipulation of the implantable component from outside the body by means of the manipulating device both on the first implantation and later.

More than one coupling element can also be arranged at the implantable component to be able to use a plurality of manipulating devices or a divided manipulating device which can, in simplified terms, also be used in this case for the alignment of the implantable component. The plurality of coupling elements at the implantable component are spaced apart from one another at the surface of the implantable component for this purpose and can also be used to be able to select the most suitable access path depending on the implantation site.

The coupling element at the component is furthermore configured for the self-retaining coupling of a manipulating device. This means that the implantable component does not have to be held tight permanently by actuation of the manipulating device as is the case, for example, with various surgical forceps. The coupling between the component and the manipulating device is advantageously designed as self-retaining so that the manipulating device can also be left out of consideration at times by the surgeon without the coupling being released.

The coupling devices are advantageously configured so that corresponding coupling forces are only developed between the coupling elements, for example by elastic deformation of one of the coupling elements, without forces being transmitted via the shaft of the manipulating device for this purpose.

The surgeon can hereby concentrate sequentially on different manipulating devices and it is ensured that the relative position of a manipulating device to the implantable component is fixed in a stable and unmovable manner.

The coupling element can be integrated in the component or fixedly connected thereto. In this respect, the coupling between the coupling element fastened to or integrated in the component and the manipulating device should advantageously also be releasable again in a particularly easy manner so that the manipulating device can be easily removed from the patient's body after the positioning and assembly of the implantable component.

The coupling element itself can in this respect, for example, be formed as an internal thread in the implantable component, preferably inside a bore and a further coupling element in the form of a threaded spigot can be screwed into it.

The coupling element can equally be designed as a bore or as a group of bores in the component into which bolts of a further coupling element can be introduced. Corresponding bolts can, for example, comprise metal, but also elastic materials such as rubber or also spring wire which can be introduced into the corresponding bores in a force-locking manner. A coupling element can typically also be designed as a groove, for example, having an undercut, for example, as a dovetail groove, into which a body of a further component which is designed in a correspondingly complementary manner can be inserted.

Bores or blind holes or other openings with or without undercuts can also form a coupling element, with the respective complementary coupling element then, for example, being able to have a deformable and/or movable body having projections and/or latching elements which effect a coupling and which can either be latched by means of an actuation device or which can be deformed then on the provision of a pulling force and the exceeding of a specific trigger force to separate the coupling elements. For this purpose, for example, one of the coupling elements can at least partly comprise an elastomer or a spring.

For example, the manipulating device can include a corresponding coupling element and additionally a hollow shaft which is coupled to a handle. The corresponding actuation member for latching noses or for releasing a screw connection in the region of the coupling between the coupling elements can be provided within the shaft and the actuation member can be actuable in the region of the handle of the manipulating device.

It is also conceivable to form a coupling element as a cone which is integrated in the component, for example, a wall of the component, and into which a further cone can be pushed which forms a second coupling element which is connected to a manipulating device. The cone surfaces can, for example, be coupled to one another by a press fit, but also by means of adhesive or by a vacuum-tight closure. Skew cone clamps can also be used for such a connection.

It is moreover conceivable that one or more wrench flats at the implantable component serve as the coupling element and allow the shape-matched engagement of a corresponding coupling element of the manipulating device. Provision can also advantageously be made that the corresponding coupling element at the component side is fastened to the implantable component, for example bonded, welded or soldered thereto or also formed in one part therewith. This can be made, for example, in that a coupling plate having a threaded bore or an eyelet or a solid body, which can in turn have a bore, a groove, wrench flats or cone surfaces, is fastened to the implantable component.

The coupling element can, for example, also be formed as a smooth, surface-smoothed area onto which a suction cup serving as a second coupling element can be placed. The suction cup can, for example, be directly aerated and vented through the shaft of the manipulating device to which it is connected in order directly to establish and release the coupling between the coupling elements.

The connection of two smooth coupling surfaces of two coupling elements by means of an adhesive is also conceivable, with the adhesive being able to be directly dissolved or embrittled to release the connection. The adhesive can, for example, be made as a thermoplastic which can be liquefied in a short time to separate the coupling elements from one another or as a curable resin which can be embrittled by radiation cross-linking, for example by UV light, so that the adhesive bond can be easily broken.

It is also conceivable to connect the implantable component to a coupling element of the manipulating device in one piece in the manufacture by casting so that the implantable component, the coupling element connected thereto and at least one part of the manipulating device itself or the total manipulating device are made in one piece, for example in an injection molding process.

A desired break point is then provided between the coupling elements of the implantable component and of the manipulating device to be able to remove the manipulating device after the positioning of the implantable component by breaking the coupling between the coupling elements.

A magnet or a ferromagnetic workpiece can, for example, be provided as a coupling element at the component side which is arranged at the outer side or in the interior of the component and which cooperates with a magnet or with a ferromagnetic part of the manipulating device for the coupling. A part of a motor or of a rotor can also act as a magnet in the component, for example. A fitting surface can be provided at the outer side of the component for the coupling of the manipulating device. One of the magnets of the coupling device can be designed as a switchable electromagnet. A corresponding fitting surface can be designed, for example when it forms a part of the coupling element at the component side, as a mechanical catching device for the second coupling element associated with the manipulating device and can have a recess which has introduction chamfers or similar introduction aids for the second coupling element. An introduction chamfer can, for example, be integrated in an introduction cone, a hollow sphere or another recess tapering toward the component interior. The second coupling element can optionally have a complementary geometrical shape.

In particular when the first coupling element is formed as a fitting surface, particularly with an introduction chamber, and in particular when the fitting surface itself is not located in direct proximity to a ferromagnetic body of the component, but also in all other cases described here, the component can be designed such that the contour of the fitting surface can be reproduced by imaging processes, for example X-rays or ultrasound. This is e.g. possible by a metal surface cover of the component in the region of the fitting surface or by a marker body which has a higher density than the wall of the component and which is integrated in the component in direct proximity of the fitting surface or with a recognizable geometrical relation to the fitting surface. A coupling can thus be established more easily and without visual contact between a manipulating device having a ferromagnetic coupling element and the component on a further invention which may become necessary after the first implantation.

An eyelet can also be provided at an outer surface of the component as a coupling element through which eyelet a thread is guided which serves as a coupling element of the manipulating device. Such a design is in particular of interest when a part of a longer flexible component such as a tubular canula should be drawn from an entry site to a target site. The coupling can then be easily separated by separation of the thread.

The associations with the component, on the one hand, and with the manipulating device, on the other hand, can generally be swapped over in the above-described complementary coupling elements.

A coupling device in accordance with the invention correspondingly provides a first coupling element which is associated with the implantable component as well as a second coupling element which is associated with the manipulating device, with the coupling elements being connectable or connected to one another in a force-locking manner and/or in a shape-matching manner and/or with material continuity.

The coupling device is in this respect advantageously configured so that the coupling is kept stable without an external effect.

If the coupling comprises a connection with material continuity between the first component and the second component, said connection can be separated by breaking, cutting or changing the mechanical material properties of at least one part of the coupling device. The change in the mechanical material properties is understood, for example, as an embrittlement by radiation effect or thermal effect or a melting of a part of the coupling or a vaporizing, for example by the effect of a laser.

The invention also relates, in addition to an implantable component, a manipulating device and a coupling device, to a corresponding system having one or more components and one or more manipulating devices which are correspondingly configured to be couplable in a simple self-retaining manner by means of the coupling elements. The corresponding couplings must also be able to be released again in a simple and gentle manner inside the patient.

The invention further also relates to a method of connecting an implantable component to a manipulating device, with the component being mechanically connected to the manipulating device before the introduction into the patient's body by means of a self-retaining releasable coupling device.

This can, for example, already take place in the manufacture of the implantable component by integration of the coupling device, in that, for example, the component and at least one part of the manipulating device are manufactured in one piece together with the coupling device in an injection molding process or are connected to one another in a joining process.

The implantable component can also be releasably screwed, clamped, bonded or latched to the manipulating device, with a respective one of the coupling elements cooperating in a complementary manner with the other coupling element and with, for example, a threaded bore being arranged in the component and a corresponding threaded bolt at the manipulating device and with each of the coupling elements also each being able to be provided in swappable manner at the respective other part. If, therefore, for example, an eyelet is provided at the implantable component and a corresponding hook at the manipulating device, the hook can also be provided at the implantable component and the eyelet at the manipulating device. This also applies to all other embodiments of the coupling elements.

If the implantable component and the manipulating device are already connected to one another before the start of a surgical procedure, this facilitates and accelerates the surgical procedure.

The separation of the implantable component from the manipulating device can typically only take place after the end of the implantation, for example by mechanical breaking of the coupling device or by another separation of the coupling device.

The coupling device can be mechanically weakened, for example, before the separation, e.g. by cooling, heating, irradiating, bending or by kinking the coupling device.

If the method for separating the implantable component from the manipulating device takes place in manner which does not provide any displacement or movement of the manipulating device with respect to the component, this has the advantage that the positioning of the component does not have to be changed again after the end of the surgical procedure. A corresponding release of the coupling device can take place, for example, by cutting or chemical dissolving, degrading, liquefying or vaporizing of a part of the coupling device.

BRIEF DESCRIPTION OF THE DRAWINGS

The invention will be shown and described in the following with reference to an embodiment in a drawing. There are shown FIG. 1 a representation of an implantable component and of two manipulating devices in a three-dimensional view;

FIG. 2 schematically in section, a manipulating device, a section of an implantable component and a coupling device;

FIG. 3 a view of a coupling device;

FIG. 4 a coupling device from FIG. 3 in a plan view;

FIG. 5 a further coupling device;

DETAILED DESCRIPTION OF THE INVENTION

Figure 6:
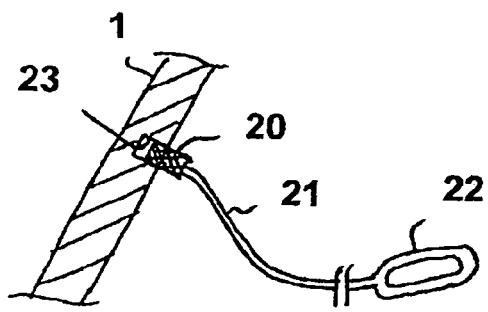
FIG. 6 a coupling device, a section of a component and a manipulating device.

FIG. 1 shows schematically and in a stylized fashion an implantable component 1, which, for example, represents a pump for conveying blood as a part of a cardiac assist system, having a cylindrical outer wall 2 of a pump housing and a axial rotor, which is not shown in detail, supported in the hollow cylinder.

A coupling element 4 of a manipulating device 5 is fastened to the end face 3 of the component 1 and is connected to a coupling element which is not shown in any more detail and which is integrated in the component 1.

The coupling element 4 is connected to a shaft 6 of the manipulating device 5 which is connected at its proximal end to a handle 7. A knob 8 is moreover provided at the handle 7 and can, for example, be connected to a core 9 which extends in a hollow space of the shaft 6 up to the coupling element 4.

The knob 8 can be moved with respect to the handle 7, for example displaced and/or rotated, to move the core 9 with respect to the shaft 6 in order thus to actuate the coupling element 4 and, for example to release the manipulating device 5 from the component 1.

A further manipulating device 5' is connected to the component 1 at another point via a further coupling element 4'. The further manipulating device 5' likewise has a handle 7' and a knob 8'. The component 1 cannot only be displaced, but also rotated by both manipulating devices 5, 5' together which are fastened at the component 1 to points spaced apart from one another.

The second manipulating device 5' can also have a core 9', which is movable by means of the knob 8', within a hollow shaft 6'.

FIG. 2 shows an exemplary implementation of a coupling device 10 at the component 1 having a blind hole which has an internal thread into which a threaded bolt 11 is screwed. The threaded bolt 11 is connected as a coupling element of the manipulating device to a core 9 which extends through a hollow shaft 6 and can be rotated therein to screw the threaded bolt 11 into or out of the threaded bore 10. The shaft 6 can thus be fastened to the component 1, which is only shown sectionally in FIG. 2, and released from it again.

Generally, a coupling element can be formed by a cut-pout, in particular a bore or a groove, having an undercut or without an undercut.

It is prevented by additional spigots at the shaft, which engage into corresponding bores of the implant, that the implant also rotates on the release of the screw connection. This moreover ensures that the implant can also be rotatingly manipulated.

A flange 72 can also be provided in the shaft 6 and can be screwed to the component 1 by means of the threaded bolt 11 and a head 73 of the threaded bolt by screwing into the threaded bore 10.

FIG. 3 schematically shows a coupling element 12 of a manipulating device in the form of a flat, plate-shaped thermoplastic end part at which a shaft 13 is engaged which forms a part of a manipulating device. The plate-shaped part 12 is connected to, the wall piece 14, for example made in a planar fashion and forming a coupling element at the component side, for example welded thereto, bonded thereto or manufactured in one piece therewith as an injection molded part. The component 1 can thus be manipulated by means of the shaft 13 until the coupling element 12 is broken off at the component by kinking the plate 12.

For better clarity, this configuration is shown in a plan view in FIG. 4, with the plate 12 and the shaft 13 being recognizable. The plate 12 can be kinked and removed by pivoting in the direction of the arrows 15, 16.

The attachment of the plate-shaped piece 12 in the wall 14 of the component 1 forms the coupling element which is integrated there and to which the kinkable part of the plate 12 is connected as a coupling element of the manipulating device.

In accordance with FIG. 5, a shaft 17 is connected to a bell-shaped coupling element 18 which is connected to the implantable component 1 by means of a short wire 19. The wire 19 provides that the bell 18 is seated on the component 1 and the component 1 can thus be moved by means of the shaft 17.

The wire 19 can be turned off or torn off by a rotation of the shaft 17 at its longitudinal axis or by a tilting of the bell part with a large expenditure of force to remove the manipulating device 17, 18 from the component 1. The coupling elements 18, 19 provide a good handling of the component 1 via the manipulating device as long as the connection exists.

In FIG. 6, a coupling device is shown having a coupling element 20 which comprises an elastomer and which is connected to a handle 22 of a manipulating device by means of a shaft 21. The element 20 is fixed in a force-locking manner in a bore 23 as a coupling element of an implementable component 1. For example, the element 20 can be heated and pressed into the bore 23 to establish a connection of the coupling device 20, 23. The manipulating device 20, 21, 22 can subsequently be removed from the component 1 by pulling at the shaft 21. It is also conceivable previously to heat the coupling element 20 or to cool it considerably to allow it to shrink.

Figure 7:
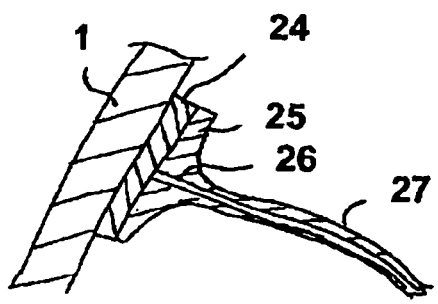
FIG. 7 a section of a component and a coupling device.

In FIG. 7, a coupling device is shown having a first component 1 onto which a coupling element in the form of a plate 24 is set, for example welded, soldered or bonded. The plate 24 can also be designed as an integrated part of the component 1.

A suction cup 25 is placed on the smooth surface of the coupling element 24 and can, for example, comprise an elastomer, but also a hard highly polished plate, for example of steel. The two plates 24, 25 adhere as coupling elements to one another in a sucking manner with a sufficient surface quality. This is in particular the case when one of the components is formed as an elastomer suction cup.

A ventilating passage 26 can be provided within the second coupling element 25; it extends through the shaft 27 and can be aerated or evacuated from the proximal end of the manipulating device 25, 26, 27 to couple or release the coupling device 24, 25.

Figure 8:
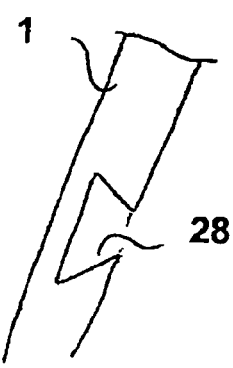
FIG. 8 a section of an implantable component.

In FIG. 8, a section of an implantable component 51 is shown schematically having a dovetail groove 28 or a bore having undercuts.

Figure 9:
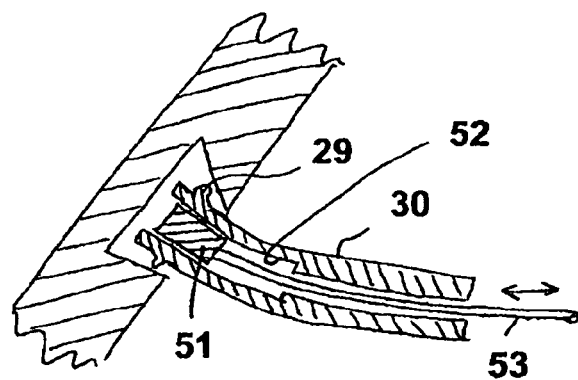
FIG. 9 a section of an implantable component with a coupling device.

If it is a radially symmetrical bore having undercuts, in accordance with FIG. 9, a tulip-like coupling element 29 having outwardly facing latching noses can thus be inserted therein which elastically latch into the undercuts of the bore 28. The coupling element 29 is connected to a shaft 30 of a manipulating device and can also only be pulled out of the bore 28 by sufficient pulling at this shaft 30 when a blocking element 51 in the form of a cylinder is spaced apart axially from the latching noses 29 within a cut-out 52 in the manipulation apparatus by means of movement of the core 53 and thus releases an inward movement of the latching noses. The shaft 30 is hollow to receive the core 53.

Figure 10:
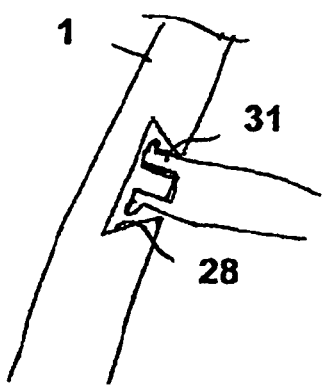
FIG. 10 an alternative coupling device to that shown in FIG. 9.

Another constellation of a coupling element 31 is shown in FIG. 10 which is equally arranged in a bore of the implantable component 1 having undercuts and which is substantially cylindrical with outwardly facing latching noses of elastically bendable end regions of end fingers of the coupling element. The coupling element 31 is also fixedly seated in the bore 28, but can be pulled out thereof by expenditure of force or by pulling in the latching noses of the coupling element 31.

Figure 11:
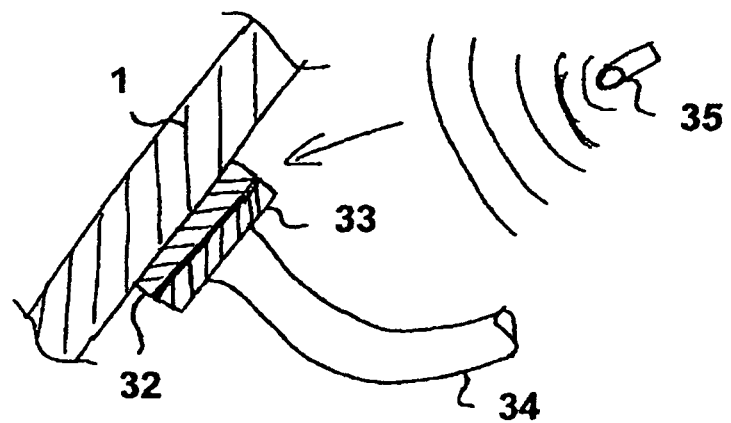
FIG. 11 a section of a component with a coupling device.

FIG. 11 shows a coupling apparatus having a first coupling element 32 and a second coupling element 33 which are each formed in plate-shape. The first coupling element 32 is fastened to a section of an implantable component 1 by bonding, welding or other joining technique and has a planar, smooth surface on the side remote from the component 1. The second coupling element 33 is laid onto the surface and is fastened there, for example, by means of an adhesive, e.g. an epoxy resin or another curable resin.

The coupling elements are thereby connected to one another and the shaft 34 of a manipulating device is connected in a fixed and self-retaining manner to the component 1 via this coupling apparatus.

The connection can be permanently established, for example, before introduction of the component 1 into a patient's body.

To release the coupling connection, the epoxy resin between the coupling elements 32, 33 can be rehardened so much, for example by means of a UV radiation source 35, that it becomes brittle so that the coupling elements 32, 33 can easily be separated from one another.

Provision can, however, also be made that the coupling elements 32, 33 are connected to one another by a thermoplastic adhesive which can be liquefied by irradiation, for example by a heat source, so that the coupling can be dissolved in this manner and the manipulating device can be removed by separation of the second coupling element 33 from the first coupling element 32. Ultrasonic pulses or laser beams can also be used to dissolve the coupling.

Figure 12:
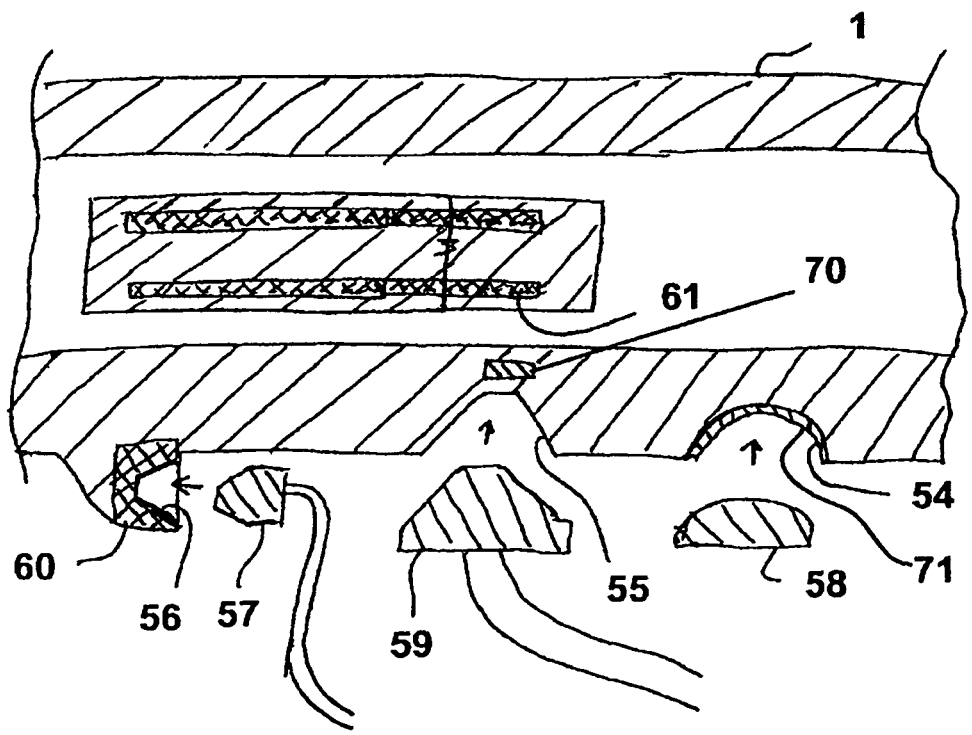
FIG. 12 a part of an implantable component in a section with a coupling device.

A constellation is shown in FIG. 12 in which a hollow cylindrical component 1 as a coupling element has, for example, a spherical fitting surface 54 and two conical fitting surfaces 55, 56. The complementary cone 57 can run into the fitting surface 56 parallel to the longitudinal axis of the cylindrical component 1; the complementary bodies 58, 59 can move radially into the other fitting surfaces. The bodies 57, 58, 59 each represent coupling elements of a manipulating device and can be formed as ferromagnetic bodies, optionally as magnets, and also as switchable electromagnets.

The fitting surfaces 54, 55, 56 can each be surrounded by ferromagnetic and/or magnetized material of the component 1, as shown for the example of the fitting surface 56 by hatching of the magnetic region 60.

Provision can also be made that the magnetic effect of magnetically effective parts 61 in the interior of the component 1, for example of parts of a pump drive or of a magnetic valve, are used for the coupling.

To facilitate a coupling of the manipulating device to the component by means of imaging processes, a marker body 70 integrated in the wall of the component or a surface coat 71 of a fitting surface 54 comprising a material of high density, in particular metal, preferably a precious metal, chromium or surgical steel, can be provided.

To release such a magnetic coupling, either a corresponding electromagnet can be switched off or the manipulation apparatus can be moved in a jerky manner. A demagnetization of the magnets by means of an alternating field can also take place. A different alignment of the magnetic poles with respect to one another can however, also be achieved by rotating the one magnet with respect to the other so that a simplified release is made possible by the magnetic repelling forces which arise.

Figure 13:
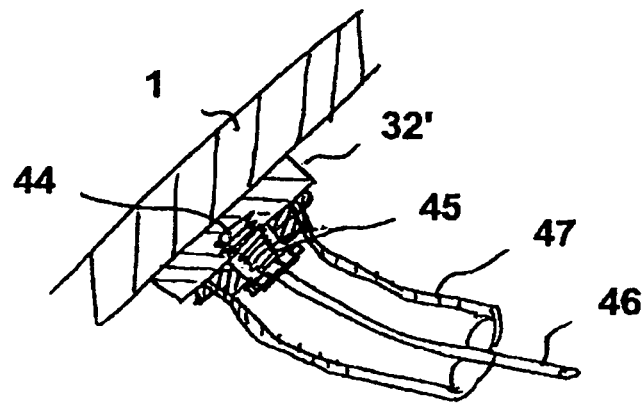
FIG. 13 a further alternative of a coupling device with a section of an implantable component.

In FIG. 13, a coupling apparatus is shown having a plate 32' which is jointed to an implantable component 1 and which has a blind bore 44 having an internal thread. The plate 32' having the blind bore 44 in this respect represents a first coupling element of the component 1. A second coupling element can be connected to this first coupling element and has a threaded bolt 45 which is connected to a core 46. The core 46 extends in the hollow space of a shaft 47 which represents a part of a manipulating device and is proximally connected to a handle not shown in FIG. 13. The shaft 47 and the core 46 are connected to the coupling element 32' of the implantable component 1 by means of the threaded bolt 44.

If the core 46 is rotated with respect to the shaft 47 via a knob at the handle of the manipulating device, the threaded bolt 45 can hereby be screwed into the plate 32' or out of it or of the threaded bore 44 in order to establish or separate the coupling depending on the situation.

In the state of an established coupling, the coupling apparatus is self-retaining, i.e. the first component 1 can easily be displaced and positioned or rotated as desired at the handle, not shown, of the manipulating device.

The threaded bolt 47 can selectively also be replaced with a nut having an internal thread connected to the core 46 and the threaded bore 44 with a corresponding threaded bolt.

As a further embodiment, the implantable component can also have a wrench flat, for example a hexagonal flat, as a coupling element to which a complementary wrench can engage as a second coupling element. If this combination is designed in a press fit, the connection is self-retaining.

Provision is advantageously made in the described coupling devices to form them at the implant at the surface not conducting blood. Any contamination or damage to the passage conducting blood can thereby be prevented. In addition, any cut-outs, bores or the like provided are not provided at the blood conducting passage so that dead flow regions are avoided.

Figure 14:
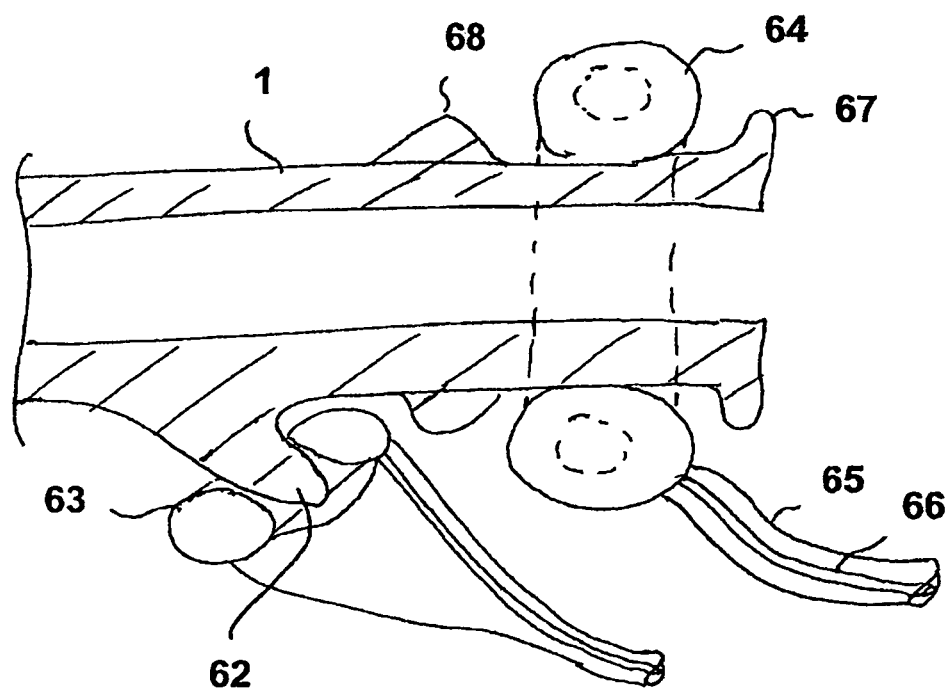
FIG. 14 an alternative of a coupling device with an inflatable coupling element.

As shown in FIG. 14, a combination of an inflatable hollow body, in particular of cushion, on the one hand, and of a gripping surface, on the other hand, can also be provided as a coupling device, for example at the component side.

For example, a cushion inflatable via the shaft of a manipulating device can be introduced into a hollow space of a component and inflated there. For this purpose, the corresponding hollow space can have an undercut. The inflatable hollow body can also be made as a torus 63, 64 and be pushed over the component 1 or a part 62 of the component and inflated there.

As soon as the implant has been positioned and aligned, the pressure in the hollow body can be reduced and the coupling apparatus thus separated.

The hollow body can be coated with an elastomer for better adhesion to the component and to save the component surfaces.

A fluid passage 66 is in each case provided in the shaft 65 of the manipulating device for inflating and pressure reducing of the hollow body. Beads 67, 68 can be provided at the component 1 for holding the hollow body which thus form corresponding fitting surfaces as a coupling element at the component side.

The component can be simply positioned and aligned by a surgeon by the different variants shown of a self-retaining coupling apparatus between an implantable component and a manipulating device without the hand of the surgeon having to be directly guided into the operating field. A comparatively small access to the operating field is thereby made possible. The connection between the instrument or the manipulating device, on the one hand, and the component, on the other hand, can already be established before the actual surgical procedure and can be dissolved after the implantation.

The manipulating device, the coupling device and the implantable component can be characterized generally by the following principles of action as special aspects of the invention:

1st aspect: the provision of fixed wrench flats at the component which cooperate with a complementary form of a coupling element;
2nd aspect: the coupling via a force locking (clamping) by an inflatable body or by a body of a coupling element spreadable in an opening;
3rd aspect: the coupling simultaneously at two points spaced apart from one another at the component, whereby the rotatability and tiltability is improved as a consequence of the separate manipulation possibilities of the coupling points;
4th aspect: the magnetic coupling of a coupling element of the manipulating device to a magnetically active part of the implantable component, in particular a drive unit, further particularly a pump unit.

The invention claimed is:

1. A manipulating device for handling a component of a system for blood conveying implantable into a patient's body, comprising:
   more than one coupling elements configured for mechanical coupling to an implantable component,
   wherein the couplings between the manipulating device and the component enable a manipulation in all spatial directions;
   wherein the coupling elements are spaced apart on the component;
   wherein the manipulating device comprises a flat plate that removably couples with a corresponding planar wall of at least one of the coupling elements.

2. The manipulating device of claim 1, wherein the more than one coupling elements are configured for self-retaining coupling of the manipulating device.

3. The manipulating device of claim 2, wherein a magnet or a ferromagnetic body is provided as one of said more than one coupling elements.

4. The manipulating device of claim 3, wherein said magnet is a switchable electromagnet.

5. A coupling device for the mechanical coupling of a component of a system for blood conveying implantable into a patient's body to a manipulating device, comprising:
   more than one coupling element associated with the implantable component and a corresponding number of coupling elements associated with the manipulating device, with the implantable component coupling elements and the manipulating device coupling elements being connectable to, and separable from, one another,
   wherein the couplings between the manipulating device and the component enable a manipulation in all spatial directions, wherein at least one of the coupling elements has an end portion with outwardly facing latching noses that are selectively locatable in an undercut bore, said latching noses being elastically deformable so said coupling element can be selectively removed from said bore;
   wherein the coupling elements are spaced apart on the component.

6. The coupling device of claim 5, wherein the coupling elements of the implantable component and the manipulating device are configured connectable to one another such that the coupling of the coupling elements is made self-retaining.

* * * * *